US012661073B2

(12) United States Patent
Cahill

(10) Patent No.: US 12,661,073 B2
(45) Date of Patent: Jun. 23, 2026

(54) REMOTE MONITORING OF A TYPE OF ARRHYTHMIA

(71) Applicant: Lexi Devices, Inc., Berkeley, CA (US)

(72) Inventor: Scott Cahill, Berkeley, CA (US)

(73) Assignee: Lexi Devices, Inc., Berkeley, CA (US)

( * ) Notice: Subject to any disclaimer, the term of this patent is extended or adjusted under 35 U.S.C. 154(b) by 195 days.

(21) Appl. No.: 18/748,106

(22) Filed: Jun. 20, 2024

(65) Prior Publication Data

US 2024/0423554 A1 Dec. 26, 2024

Related U.S. Application Data

(60) Provisional application No. 63/522,128, filed on Jun. 20, 2023.

(51) Int. Cl.
*A61B 5/00* (2006.01)
*A61B 5/11* (2006.01)

(52) U.S. Cl.
CPC .......... *A61B 5/7282* (2013.01); *A61B 5/0002* (2013.01); *A61B 5/1117* (2013.01); *A61B 5/7228* (2013.01); *A61B 5/7253* (2013.01); *A61B 5/7267* (2013.01); *A61B 5/742* (2013.01); *A61B 2560/045* (2013.01)

(58) Field of Classification Search
CPC .......... A61B 2560/045; A61B 15/0002; A61B 15/024; A61B 15/0507; A61B 15/1117;

A61B 15/7228; A61B 15/7253; A61B 15/7264; A61B 15/7267; A61B 15/7282; A61B 15/742
See application file for complete search history.

(56) References Cited

U.S. PATENT DOCUMENTS

2020/0367784 A1* 11/2020 Cho ...................... G01S 7/2923

* cited by examiner

*Primary Examiner* — Michael T Rozanski
(74) *Attorney, Agent, or Firm* — Steven Stupp

(57) ABSTRACT

During operation, a measurement sensor in an electronic device may perform radar measurements associated with an individual, where the radar measurements include information corresponding to a physiological signal of the individual. Then, the electronic device may analyze the radar measurements to extract an amplitude and/or a phase of chest motion on or proximate to an anterior surface and/or a posterior surface of the individual. Moreover, the electronic device may map an amplitude and/or a phase of the chest motion on or proximate to the anterior surface and/or the posterior surface to one or more anatomical locations associated with an organ of the individual. Next, the electronic device may detect whether the type of arrhythmia is present based at least in part on the mapped amplitude and/or the phase.

20 Claims, 6 Drawing Sheets

AMPLITUDE
AND/OR
PHASE
410

MAPPING
412

ANATOMICAL
LOCATIONS
414

HEART
416

REMOTE MONITORING OF A TYPE OF ARRHYTHMIA

CROSS REFERENCE TO RELATED APPLICATIONS

This application claims priority under 35 U.S.C. 119(e) to U.S. Provisional Application Ser. No. 63/522,128, "Remote Monitoring of a Type of Arrhythmia," by Scott Cahill, filed on Jun. 20, 2023, the contents of which are herein incorporated by reference.

FIELD

The described embodiments relate to techniques for remotely assessing an individual for the presence of a type of arrhythmia or irregular heartbeat, e.g., using radar measurements.

BACKGROUND

A physiological signal (e.g., a signal corresponding to a physiological response) associated with an individual can be analyzed to extract the physiological response, such as a vital sign of the individual. For example, a Fourier transform can be used to convert a time-domain signal corresponding to breathing to the frequency domain in order to identify a respiration rate of the individual.

Physiological signals are often measured using direct contact with an individual. Sometimes physiological signals are measured remotely or at a distance from the individual.

However, it is often difficult to remotely assess irregularities in the physiological response of the individual. For example, it is often difficult to remotely measure an arrhythmia or irregular heartbeat of the individual.

SUMMARY

An electronic device that remotely assesses an individual for a presence of a type of arrhythmia or irregular heartbeat is described. This electronic device includes: a measurement sensor; a computation device (such as a processor, a processor core, a graphics processing unit, etc.) that executes program instructions; and memory that stores the program instructions. During operation, the measurement sensor performs radar measurements associated with an individual, where the radar measurements include information corresponding to a physiological signal of the individual. Then, the electronic device analyzes the radar measurements to extract an amplitude and/or a phase of chest motion on or proximate to an anterior surface and/or a posterior surface of the individual. Moreover, the electronic device maps an amplitude and/or a phase of the chest motion on or proximate to the anterior surface and/or the posterior surface to one or more anatomical locations associated with an organ of the individual. Next, the electronic device detects whether the type of arrhythmia is present based at least in part on the mapped amplitude and/or the phase.

Note that the physiological signal may include a vital sign of the individual (such as a pulse rate and/or a respiration rate of the individual).

Moreover, the type of arrhythmia may include: atrial fibrillation, tachycardia, bradycardia, a type of heart attack, etc.

Furthermore, the radar measurements may be associated with the anterior surface and/or the posterior surface of the individual. The measurement sensor may include one or more radar sensors or radar transducers, which may be at different locations and may have different transmission directions. The one or more radar sensors may be used to perform the radar measurements.

Additionally, the radar measurements may be performed synchronously, so that the amplitude and/or the phase of chest motion on or proximate to the anterior surface and/or the posterior surface of the individual can be measured and compared. In some embodiments, synchronous measurements may be performed with a time accuracy or difference on or proximate to the anterior surface and/or the posterior surface of less than a predefined amount (such as 0.001, 0.01 or 0.1) of the pulse rate of the individual.

Note that the analysis may include demodulating the radar measurements to obtain the physiological signal of the individual. Consequently, the analysis may include: amplitude modulation, frequency modulation, phase modulation, a Fourier Transformation, etc.

In some embodiments, the analysis may be performed by the electronic device. Alternatively, in some embodiments, the analysis may be performed by a (separate, e.g., remotely located) computer system. For example, the electronic device may include an interface circuit that communicates second information specifying the radar measurements to the computer system. Then, the computer system may perform the analysis and may communicate third information specifying the physiological signal to the electronic device.

Moreover, the organ may include the heart. For example, the measured amplitude and/or the phase on or proximate to the anterior surface and/or the posterior surface of the individual may be mapped to one or more anatomical locations associated with the heart of the individual. In some embodiments, the mapping may represent a three-dimensional transformation.

Furthermore, when the type of arrhythmia is detected, the electronic device may provide fourth information specifying the type of arrhythmia. In some embodiments, the providing of the fourth information may include displaying a graphical representation of the mapping to the one or more anatomical locations.

Additionally, the mapping may be performed using a pretrained predictive model, such as: a pretrained neural network or, more generally, a pretrained supervised-learning model. In some embodiments, spatial patterns of the amplitude and/or the phase on or proximate to the anterior surface and/or the posterior surface may be input to the pretrained neural network, and the output of the pretrained neural network may include whether or not the arrhythmia is presence and/or the type of the arrhythmia. Note that the output may indicate a confidence (such as a confidence interval) of the detected presence of and/or the type of the arrhythmia. Thus, the mapping and the determination may be performed by a pretrained neural network.

Note that the measurements may be in one or more bands of frequencies. For example, the radar signals may have one or more carrier or fundamental frequencies between 300 MHz and 100 GHz.

Moreover, in some embodiments, the electronic device may detect a type of fall by the individual. For example, the electronic device may detect whether the individual has fallen (such as onto the ground) and/or whether the fall was forward (anterior), backward (posterior), to the side (lateral), etc. In some embodiments, the electronic device may determine whether the individual attempted to break or arrest their fall using, e.g., their arm, whether they hit their head when they fell, and/or how fast they were moving when their fall was arrested (e.g., by the ground or a piece of furniture).

Thus, the radar measurements may allow the electronic device to determine a probability that the individual was injured in the fall.

Another embodiment provides the computer system.

Another embodiment provides a computer-readable storage medium for use in conjunction with the electronic device or the computer system. This computer-readable storage medium includes the program instructions for at least some of the operations performed by the electronic device or the computer system.

Another embodiment provides a method for remotely assessing an individual for a presence of a type of arrhythmia or an irregular heartbeat. The method includes at least some of the aforementioned operations performed by the electronic device or the computer system.

This Summary is provided for purposes of illustrating some exemplary embodiments, so as to provide a basic understanding of some aspects of the subject matter described herein. Accordingly, it will be appreciated that the above-described features are only examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE FIGURES

The included drawings are for illustrative purposes and serve only to provide examples of possible structures and arrangements for the disclosed systems and techniques. These drawings in no way limit any changes in form and detail that may be made to the embodiments by one skilled in the art without departing from the spirit and scope of the embodiments. The embodiments will be readily understood by the following detailed description in conjunction with the accompanying drawings, wherein like reference numerals designate like structural elements.

Note that like reference numerals refer to corresponding parts throughout the drawings. Moreover, multiple instances of the same part are designated by a common prefix separated from an instance number by a dash.

DETAILED DESCRIPTION

Figure 1:
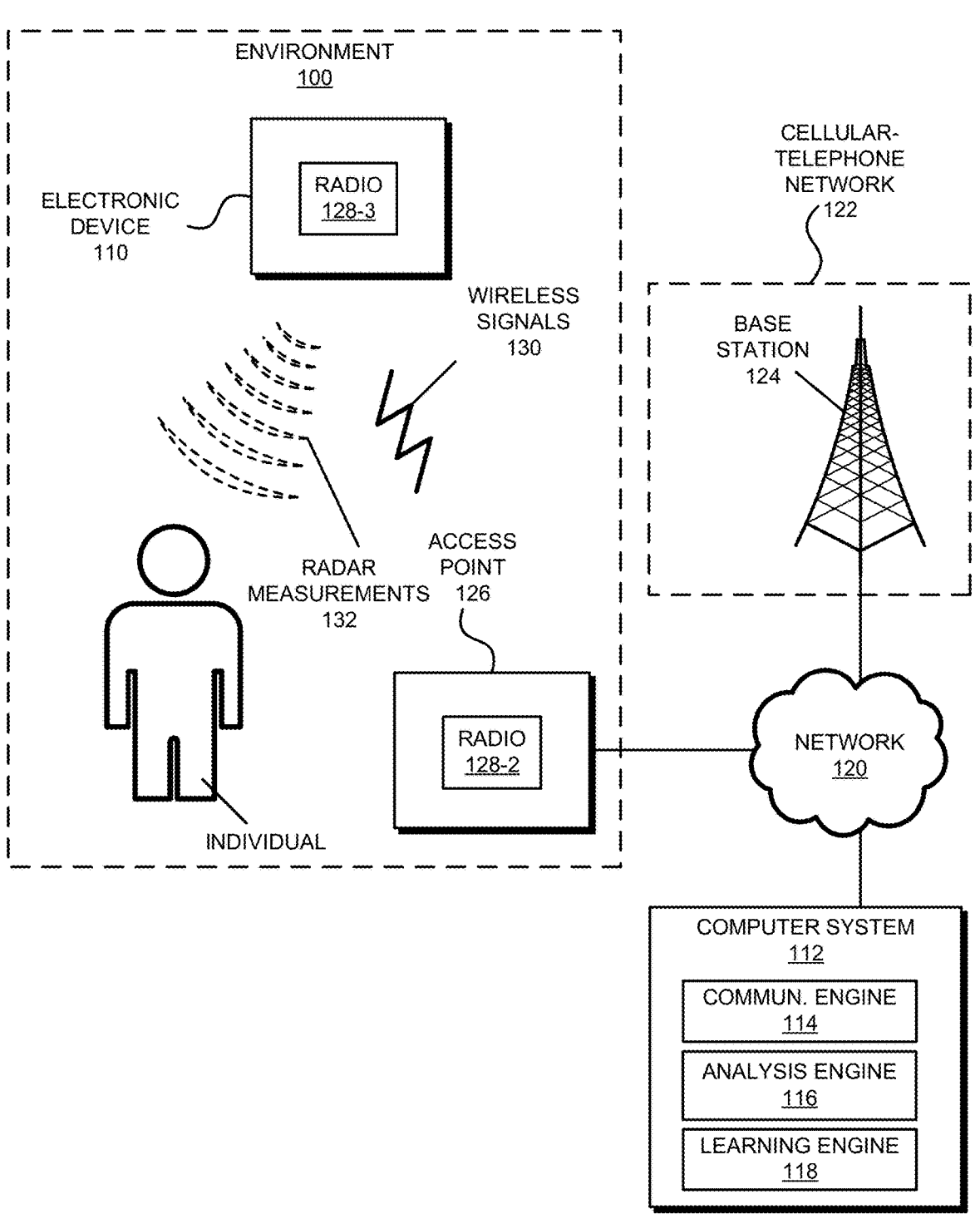
FIG. 1 is a drawing illustrating an example of a system in accordance with an embodiment of the present disclosure.

An electronic device that remotely assesses an individual for a presence of a type of arrhythmia or irregular heartbeat is described. This electronic device may include: a measurement sensor; a computation device (such as a processor, a processor core, a graphics processing unit, etc.) that executes program instructions; and memory that stores the program instructions. During operation, the measurement sensor may perform radar measurements associated with an individual, where the radar measurements include information corresponding to a physiological signal of the individual. Then, the electronic device may analyze the radar measurements to extract an amplitude and/or a phase of chest motion on or proximate to (such as within 1, 3, or 10 cm of) an anterior surface and/or a posterior surface of the individual. Moreover, the electronic device may map an amplitude and/or a phase of the chest motion on or proximate to the anterior surface and/or the posterior surface to one or more anatomical locations associated with an organ of the individual. Next, the electronic device may detect whether the type of arrhythmia is present based at least in part on the mapped amplitude and/or the phase.

By detecting whether the type of arrhythmia or the irregular heartbeat is present, these measurement techniques may allow remote monitoring of the individual. Notably, the measurement techniques may remotely detect an arrhythmia or irregular heartbeat of the individual. These capabilities may facilitate improved medical care of the individual. For example, the measurement techniques may facilitate remedial action when the arrhythmia is present, such as: providing a report or notification to a medical provider; notifying emergency services (such as contacting 9-1-1); and/or taking corrective action to eliminate the arrhythmia (such as having a medical provider or professional prescribe a medication, applying a corrective electric shock using a defibrillator, etc.). Consequently, the measurement techniques may reduce or eliminate mortality or morbidity associated with the type of arrhythmia.

In the discussion that follows, the measurement techniques may be used by: the individual; a type of organization (such as a business, e.g., a for-profit corporation, a non-profit corporation or another type of business entity), a group (or a cohort) of individuals, a sole proprietorship, a government agency, a partnership, etc.

Furthermore, the radar measurements may include: a two-dimensional (2D) image, a 2.5D image, a 3D image (e.g., with stereoscopic information or a hologram), etc. In some embodiments, an image may be compatible with a wide variety of different resolutions and/or file formats, such as JPEG, a Tagged Image File Format (TIFF), a Graphics Interchange Format (GIF), a bitmap file format (such as BMP), a Portable Network Graphics (PNG) file format, another file format, etc.

In the discussion that follows, note that 'dynamic' may indicate time-varying.

Additionally, in the discussion that follows, electronic devices and/or components in the computer (or a computer system) may communicate using a wide variety of communication protocols. For example, the communication may involve wired or wireless communication. Consequently, the communication protocols may include one or more of: an Institute of Electrical and Electronics Engineers (IEEE) 802.11 standard (which is sometimes referred to as 'Wi-Fi®,' from the Wi-Fi Alliance of Austin, Texas), Bluetooth™ (from the Bluetooth Special Interest Group of Kirkland, Washington), Bluetooth Low Energy or BLE (from the Bluetooth Special Interest Group of Kirkland, Washington), Zigbee (from the Zigbee Alliance of Davis, California), Z-Wave (from Sigma Designs, Inc. of Fremont, California), LoRaWAN (from the Lora Alliance of Beaverton, Oregon), Thread (from the Thread Group of San Ramon, California), IPv6 over low-power wireless personal area networks or 6LoWPAN (from the Internet Engineering Taskforce of Fremont, California), another type of wireless interface, a cellular-telephone communication protocol (e.g., a 3G/4G/5G communication protocol, such as UMTS, Long Term Evolution or LTE, LTE Advanced or LTE-A, or another present or future developed advanced cellular communication protocol), an IEEE 802.3 standard (which is sometimes referred to as 'Ethernet'), 900 MHz of the ISM band, or another present or future developed wireless or wired communication protocol. In the discussion that follows, Ethernet, a cellular-telephone communication protocol, Wi-Fi and/or BLE are used as illustrative examples.

Communication among electronic devices is shown in FIG. 1, which presents a block diagram illustrating an example of a system in an environment 100. The system may include: an electronic device 110, and/or a computer system 112 (such as a server or a computer in a cloud-based computer system). During operation, a mobile application or app executing on electronic device 110 (such as a computer and/or a portable electronic device, e.g., a cellular telephone) may perform at least some of the operations in the measurement techniques. Moreover, computer system 112 may include: a communication engine (CE) 114 (or module), analysis engine (AE) 116 (or module); and/or learning engine (LE) 118 (or module).

Note that components in the system may communicate with each other via a network 120 (such as the Internet), an optional cellular-telephone network 122 (e.g., via an optional base station 124) and/or a wireless local area network or WLAN (e.g., via an optional access point 126, such as a physical access point or a virtual access point that is implemented using software). Thus, the communication may involve wired and/or wireless communication. In embodiments where the communication involves wireless communication, the wireless communication includes: transmitting advertising frames on wireless channels, detecting another component in the system by scanning wireless channels, establishing connections (for example, by transmitting association requests), and/or transmitting and receiving packets.

Figure 5:
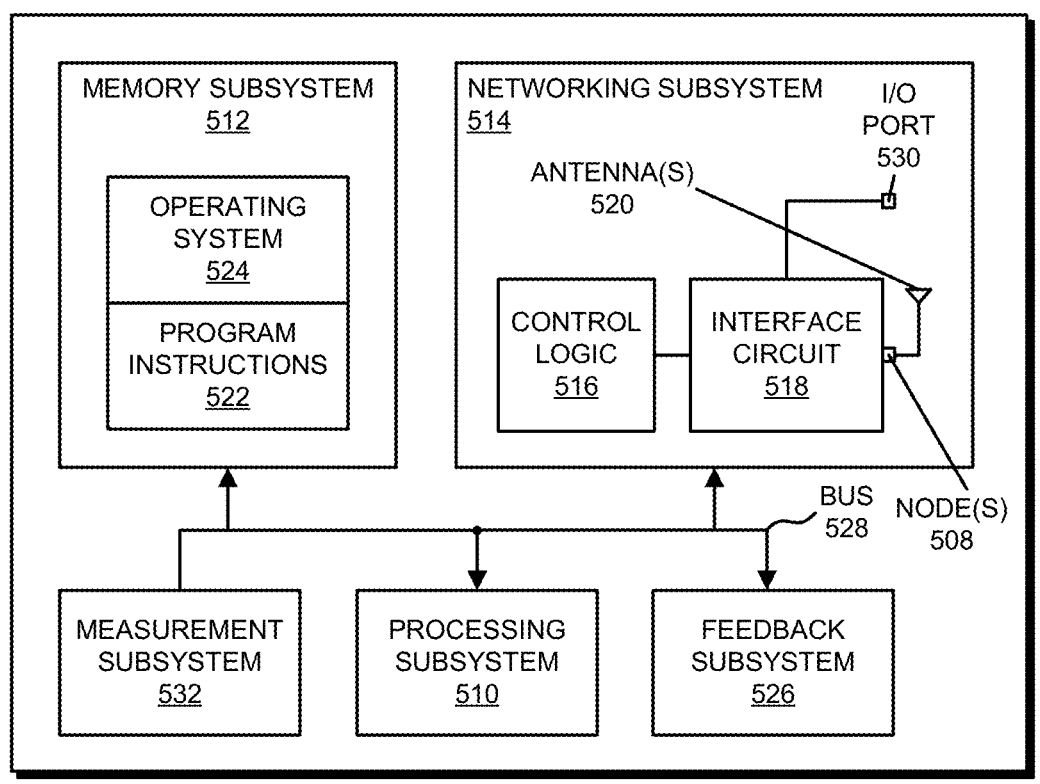
FIG. 5 is a block diagram illustrating an electronic device in accordance with an embodiment of the present disclosure.

As described further below with reference to FIG. 5, electronic device 110, computer system 112, optional base station 124 and/or optional access point 126 may include subsystems, such as a networking subsystem, a memory subsystem and a processor subsystem. In addition, electronic device 110, optional base station 124 and/or optional access point 126 may include radios 128 in the networking subsystems. More generally, the components can include (or can be included within) any electronic devices with the networking subsystems that enable these components to communicate with each other. Note that wireless communication can comprise transmitting advertisements on wireless channels to enable a pair of components to make initial contact or detect each other, followed by exchanging subsequent data/management frames (such as association requests and responses) to establish a connection, configure security options (e.g., Internet Protocol Security), transmit and receive packets or frames via the connection, etc.

Moreover, as can be seen in FIG. 1, wireless signals 130 (represented by a jagged line) are transmitted by radios 128 in components in FIG. 1. For example, radio 128-1 in electronic device 110 may transmit information (such as packets) using wireless signals. These wireless signals may be received by one or more radios 128 in one or more of the other components, such as by optional base station 124 or optional access point 126. This may allow electronic device 110 to communicate information to computer system 112, optional base station 124 and/or optional access point 126.

In the described embodiments, processing a packet or frame in a component may include: receiving the wireless signals with the packet or frame; decoding/extracting the packet or frame from the received wireless signals to acquire the packet or frame; and processing the packet or frame to determine information contained in the packet or frame.

Note that the communication between at least any two of the components in the system may be characterized by one or more of a variety of performance metrics, such as: a received signal strength indication (RSSI), a data rate, a data rate for successful communication (which is sometimes referred to as a 'throughput'), an error rate (such as a retry or resend rate), a mean-square error of equalized signals relative to an equalization target, intersymbol interference, multipath interference, a signal-to-noise ratio, a width of an eye pattern, a ratio of number of bytes successfully communicated during a time interval (such as 1-10 s) to an estimated maximum number of bytes that can be communicated in the time interval (the latter of which is sometimes referred to as the 'capacity' of a communication channel or link), and/or a ratio of an actual data rate to an estimated data rate (which is sometimes referred to as 'utilization'). In some embodiments, the communication in FIG. 1 may include or may use: multiple-input, multiple-output (MIMO) and/or orthogonal frequency division multiple access (OFDMA).

Electronic device 110 may include one or more measurement sensors (such as an imaging sensor or a camera, a microphone, a radar sensor or transducer, etc.) that perform measurements of sensor data in environment 100, such as acquiring or measuring: an image, video, sound, speech, brightness, light color, locations of one or more objects in environment 100, radar measurements 132, etc. For example, the measurements may include radar measurements 132 associated with an individual. The sensor data may be analyzed, e.g., using an image-analysis technique or a pretrained predictive model (such as a pretrained predictive model, e.g., a pretrained supervised-learning model or a pretrained neural network), to determine information, such as: identify one or more individuals, identify a voice or verbal command from speech, determine a location in environment 100, a physiological signal (e.g., a signal corresponding to a physiological response, such as a vital sign) associated with an individual. Note that a location in environment 100 may be determined using: a local positioning system, a global positioning system, wireless ranging, wireless signals, triangulation and/or trilateration.

In some embodiments, the image-analysis technique may determine features from one or more images. For example, the image-processing technique may determine the features using: a discrete Fourier transform, principal component analysis and/or a JPEG analysis. Moreover, the features may be determined using: an edge or a line-segment detector, a texture-based feature detector, a texture-less feature detector, a scale invariant feature transform (SIFT)-like object-detector, a speed-up robust-features (SURF) detector, a binary-descriptor (such as ORB) detector, a binary robust invariant scalable keypoints (BRISK) detector, a fast retinal keypoint (FREAK) detector, a binary robust independent elementary features (BRIEF) detector, a features from accelerated segment test (FAST) detector, a motion detector (such as a Gaussian-mixture model), etc. More generally, the features may be determined using a feature extraction technique.

Furthermore, the analysis may include or may use a pretrained predictive model, such as a pretrained neural network (such as a convolutional neural network, a generative adversarial network, long short-term memory or LSTM, or another type of neural network) or a machine-learning model. For example, in the measurement techniques, one or more images and/or features in the one or more images are input to the pretrained neural network, which provides an output. Alternatively or additionally, spatial patterns of the amplitude and/or the phase on or proximate to an anterior surface and/or a posterior surface may be input to the pretrained neural network, and the output of the pretrained neural network may include whether or not an arrhythmia is presence and/or a type of the arrhythmia.

Moreover, an output may be determined using a classifier or a regression model that was trained using a supervised learning technique (such as a support vector machine, a classification and regression tree, logistic regression, LASSO, linear regression and/or another linear or nonlinear supervised-learning technique). Alternatively or additionally, the analysis may use an unsupervised learning technique, such as a clustering technique.

Note electronic device 110 may be able to access and/or leverage additional information provided, directly or indirectly, by electronic device 110 and/or computer system 112. For example, electronic device 110 may provide: a timestamp, a weather condition, an acceleration measurement (which may indicate motion of the individual), sound made by the individual (such crying out, moaning, a sound corresponding to pain, or calling for help), information specifying an age of the individual, information specifying a health condition or medical history of the individual, a prescription used by the individual (such as an anti-coagulant or a blood thinner), etc.

Moreover, the information and/or the additional information may be used as inputs to a pretained predictive model (such as a pretrained supervised-learning model, e.g., a pretrained machine-learning model or a pretrained neural network), which may provide an output (such as whether or not an arrhythmia is presence and/or a type of the arrhythmia).

In general, different embodiments may implement the functionality in the measurement techniques in hardware and/or software, as is known to one of skill in the art. For example, in some embodiments, the measurement techniques may be implemented using program instructions or software that is executed in an environment on electronic device 110 and/or computer system 112, such as: an application executed in the operating system of electronic device 110 and/or computer system 112, as a plugin for a Web browser, or an application tool that is embedded in a web page and that executes in a virtual environment of the Web browser (e.g., in a client-server architecture). Note that the software may be a standalone application or a portion of another application that is resident on and that executes on electronic device 110 and/or computer system 112 (such as a software application that is provided by electronic device 110 and/or computer system 112, or that is installed on and that executes on electronic device 110 and/or computer system 112).

Alternatively or additionally, in some embodiments, software executing in an environment on electronic device 110 may interact, via network 120 with computer system 112. Then, as described further below, computer system 112 may perform at least some of the operations in embodiments of the measurement techniques. For example, electronic device 110 may provide, to computer system 112, the physiological response or the amplitude and/or the phase on or proximate to the anterior surface and/or the posterior surface. In some embodiments, computer system 112 may optionally analyze the radar measurements to extract the amplitude and/or the phase of chest motion on or proximate to the anterior surface and/or the posterior surface of the individual. Then, computer system 112 may map the amplitude and/or the phase of the chest motion on or proximate to the anterior surface and/or the posterior surface to one or more anatomical locations associated with an organ of the individual. Moreover, computer system 112 may detect whether the type of arrhythmia is present and/or the type of the arrhythmia based at least in part on the mapped amplitude and/or the phase. Next, computer system 112 may provide, to electronic device 110, information indicating or specifying whether the type of arrhythmia is present and/or the type of the arrhythmia. Based at least in part on the information, electronic device 110 may perform a remedial action, such as: providing or displaying the information, contacting or alerting a medical professional or 9-1-1, providing an instruction for a remedial action (such as providing an instruction to a defibrillator to administer an electric shock to correct the arrhythmia and restore sinus rhythm, etc. Thus, the measurement techniques may be implemented locally (e.g., in proximity to the individual) and/or remotely (e.g., using a cloud-based computer system) in the system. Moreover, in some embodiments, the measurement techniques may be implemented centrally (e.g., by a single electronic device or computer system) or in a distributed manner.

In some embodiments, electronic device 110 remotely assesses the individual for the presence of the type of arrhythmia or irregular heartbeat. During operation, a measurement sensor (such as a radar sensor or transducer) may perform radar measurements associated with the individual, where the radar measurements include information corresponding to a physiological signal of the individual (e.g., a vital sign, such as a pulse rate and/or a respiration rate of the individual). Note that radar signals that are reflected off of the individual may include modulation that encodes the physiological signal. Then, electronic device 110 may analyze the radar measurements to extract an amplitude and/or a phase of chest motion on or proximate to the anterior surface and/or the posterior surface of the individual (such as at least a portion of the front chest or the back chest). In some embodiments, the physiological signal can be analyzed to determine the physiological response, e.g., one or more vital signs, such as the pulse or respiration rate of the individual.

Moreover, electronic device 110 may maps the amplitude and/or the phase of the chest motion on or proximate to the anterior surface and/or the posterior surface to one or more anatomical locations associated with an organ of the individual (such as the heart of the individual). For example, the mapping may represent a three-dimensional transformation. Next, electronic device 110 may detect whether the type of arrhythmia is present and/or may determine a type of arrhythmia (such as atrial fibrillation, tachycardia, bradycardia, a type of heart attack, etc.) based at least in part on the mapped amplitude and/or the phase.

Note that the radar signals used in measurements 132 may be in one or more bands of frequencies. For example, the radar signals may have one or more carrier or fundamental frequencies between 5-10 GHz. More generally, the radar signals may have one or more carrier or fundamental frequencies between 300 MHz and 100 GHz. For example, the radar signals may have fundamental frequencies between 2.5 GHz (which penetrate clothing and tissue) and 60 GHz (which is largely blocked or reflected by the human body). In some embodiments, the radar signals may include or may be compatible with ultra-wideband (which is sometimes referred to as UWB or 'pulse radio'). Thus, the radar signals may include continuous and/or pulsed signals (such as frequency modulated continuous wave or FMCW signals). However, radar measurement of the physiological response of the individual is used as an illustrative example of the measurement techniques. In other embodiments, a variety of different measurement techniques may be used to measure the physiological response of the individual, such as: ultrasound, optical, etc.

Furthermore, in some embodiments, one or more of the one or more sensors in electronic device 110 may be used to detect a type of fall by the individual. For example, the measurement techniques may determine not only whether the individual has fallen (such as onto the ground), but whether the fall was forward (anterior), backward (posterior), to the side (lateral), etc. In some embodiments, the measurement techniques may determine whether the individual attempted to break or arrest their fall using, e.g., their arm, whether they hit their head when they fell, how fast they were moving when their fall was arrested (e.g., by the ground or a piece of furniture), whether they lost consciousness (and, if yes, for how long), etc. Thus, the measurement techniques may compute or determine a probability that the individual was injured in the fall (such as whether the individual likely suffered a broken bone, a concussion, another type of head injury, etc.) and, if yes, how serious the injury may be. In some embodiment, this assessment is based at least in part on the additional information and may be performed by electronic device 110 and/or computer system 112.

In these ways, the measurement techniques may detect whether the type of arrhythmia or the irregular heartbeat is present and/or may determine the type of arrhythmia. These capabilities may facilitate improved monitoring and/or medical care of the individual. Consequently, the measurement techniques may reduce or eliminate mortality or morbidity associated with the type of arrhythmia and/or may improve the quality of life of the individual.

Figure 2:
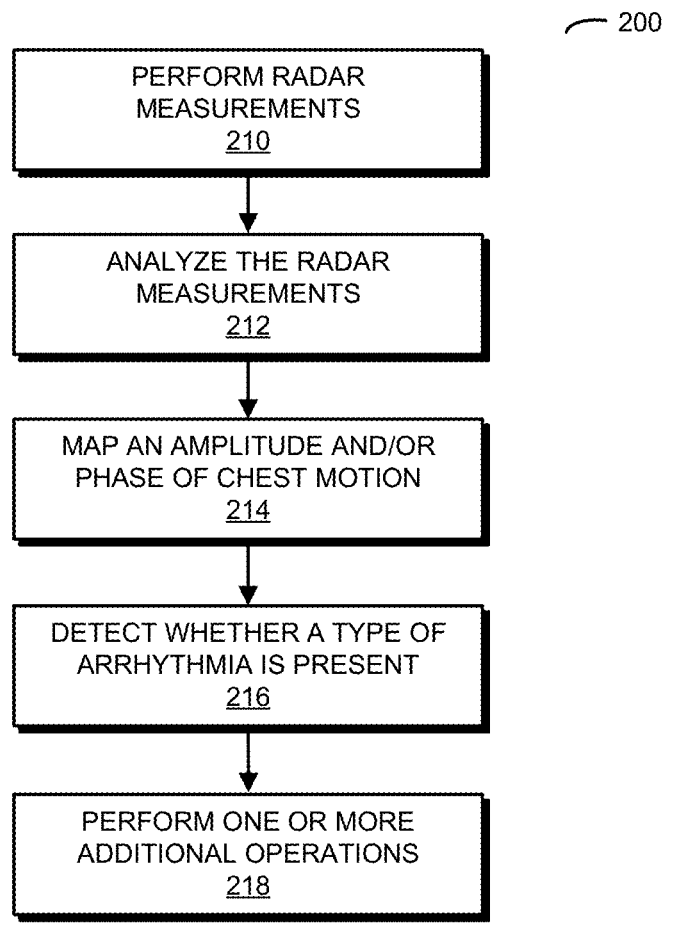
FIG. 2 is a flow diagram illustrating an example method for remotely assessing an individual for a presence of a type of arrhythmia or irregular heartbeat in accordance with an embodiment of the present disclosure.

FIG. 2 presents embodiments of a flow diagram illustrating method 200 for remotely assessing an individual for a presence of a type of arrhythmia or irregular heartbeat, which may be performed by an electronic device (such as electronic device 110 and/or computer system 112 in FIG. 1). Notably, the electronic device may include a computation device that performs method 200. For example, the computation device may include one or more of: a processor, one or more cores in a second processor, or another type of device that performs computation (such as one or more graphics processing units or GPUs, which may implement a neural network).

During operation, the electronic device may perform radar measurements (operation 210) associated with an individual, where the radar measurements include information corresponding to a physiological signal of the individual. Then, the electronic device may analyze the radar measurements (operation 212) to extract an amplitude and/or a phase of chest motion on or proximate to an anterior surface and/or a posterior surface of the individual. For example, the analysis may include demodulating the physiological response of the individual from the radar measurements. Consequently, the analysis may include: amplitude modulation, frequency modulation, phase modulation, a Fourier Transformation (such as a Discrete Fourier Transform), a wavelet decomposition, etc.

Moreover, the electronic device may map an amplitude and/or a phase of the chest motion (operation 214) on or proximate to the anterior surface and/or the posterior surface to one or more anatomical locations associated with an organ of the individual. Next, the electronic device may detect whether the type of arrhythmia is present (operation 216) based at least in part on the mapped amplitude and/or the phase.

Note that the physiological signal may include a vital sign of the individual (such as a pulse rate and/or a respiration rate of the individual). Moreover, the type of arrhythmia may include: atrial fibrillation, tachycardia, bradycardia, a type of heart attack, etc.

Furthermore, the radar measurements may be performed on or may be associated with the anterior surface and/or the posterior surface of the individual. The measurement sensor may include one or more radar sensors or radar transducers (such as 1-4 radar sensor or radar transducers), which may be at different locations and may have different transmission directions. The one or more radar sensors may be used to perform the radar measurements.

Additionally, the radar measurements may be performed synchronously (e.g., as a function of time, such as at a common portion of a cardiac cycle), so that the amplitude and/or the phase of chest motion on or proximate to the anterior surface and/or the posterior surface of the individual can be measured and compared. In some embodiments, synchronous measurements may be performed with a time accuracy or difference on or proximate to the anterior surface and/or the posterior surface of less than a predefined amount (such as 0.001, 0.01 or 0.1) of the pulse rate of the individual. For example, the pulse of the individual may be used to gate or synchronize the radar measurements.

Note that the analysis (operation 212) may include demodulating the radar measurements to obtain the physiological signal of the individual. Consequently, the analysis may include: amplitude modulation, frequency modulation, phase modulation, a Fourier Transformation, etc.

In some embodiments, the analysis (operation 212) may be performed by the electronic device. Alternatively, in some embodiments, the analysis may be performed by a (separate, e.g., remotely located) computer system. For example, the electronic device may include an interface circuit that communicates second information specifying the radar measurements to the computer system. Then, the computer system may perform the analysis and may communicate third information specifying the physiological signal to the electronic device.

Moreover, the organ may include the heart. For example, the measured amplitude and/or the phase on or proximate to the anterior surface and/or the posterior surface of the individual may be mapped to one or more anatomical locations associated with the heart of the individual. In some embodiments, the mapping may represent a three-dimensional transformation. Thus, the resulting mapped amplitude and/or the phase on the anatomy of the heart of the individual may be used to determine the presence of the type of arrhythmia and/or to determine the type of arrhythmia.

Additionally, the mapping (operation 214) may be performed using a pretrained predictive model, such as: a pretrained neural network or, more generally, a pretrained supervised-learning model. In some embodiments, spatial patterns of the amplitude and/or the phase on or proximate to the anterior surface and/or the posterior surface may be input to the pretrained neural network, and the output of the pretrained neural network may include whether or not the arrhythmia is presence and/or the type of the arrhythmia.

Note that the output may indicate a confidence (such as a confidence interval) of the detected presence of and/or the type of the arrhythmia. In some embodiments, the output may indicate a confidence (such as a confidence interval) of the detected presence of and/or the type of the arrhythmia. Thus, the mapping and the determination may be performed by a pretrained neural network.

Note that the measurements may be in one or more bands of frequencies. For example, the radar signals may have one or more carrier or fundamental frequencies between 300 MHz and 100 GHz.

In some embodiments, the electronic device optionally performs one or more additional operations (operation 218). For example, when the type of arrhythmia is detected, the electronic device may provide fourth information specifying the type of arrhythmia. In some embodiments, the providing of the fourth information may include displaying a graphical representation of the mapping to the one or more anatomical locations.

Moreover, in some embodiments, the electronic device may detect a type of fall by the individual. For example, the electronic device may detect whether the individual has fallen (such as onto the ground) and/or whether the fall was forward (anterior), backward (posterior), to the side (lateral), etc. In some embodiments, the electronic device may determine whether the individual attempted to break or arrest their fall using, e.g., their arm, whether they hit their head when they fell, and/or how fast they were moving when their fall was arrested (e.g., by the ground or a piece of furniture). Thus, the radar measurements may allow the electronic device to determine a probability that the individual was injured in the fall.

In some embodiments of method 200, there may be additional or fewer operations. Furthermore, there may be different operations. Moreover, the order of the operations may be changed, and/or two or more operations may be combined into a single operation.

Figure 3:
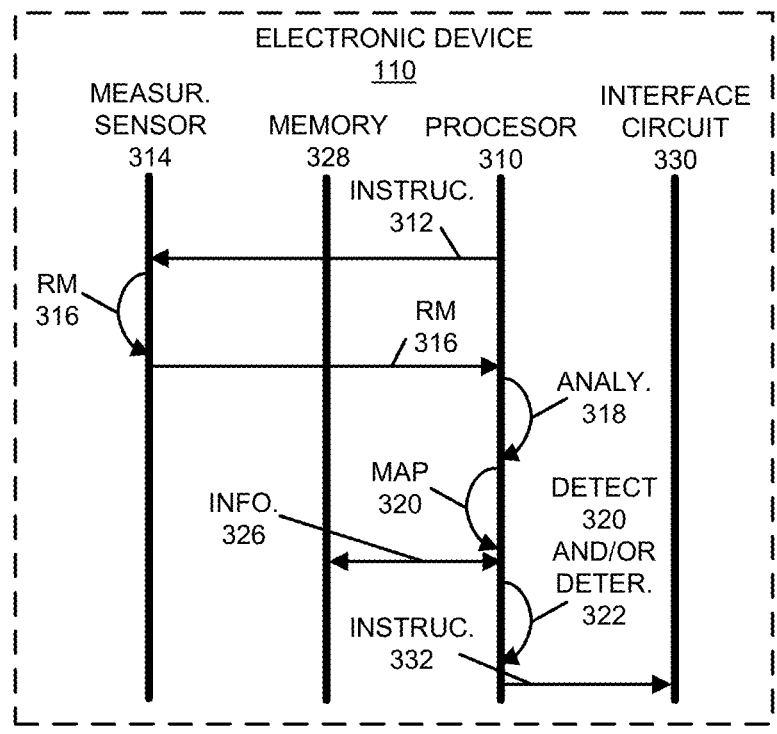
FIG. 3 is a drawing illustrating an example of communication among components in the system in FIG. 1 in accordance with an embodiment of the present disclosure.

Embodiments of the measurement techniques are further illustrated in FIG. 3, which presents a drawing illustrating communication among electronic device 110 and computer system 112. Notably, during the measurement techniques, a processor 310 in electronic device 110, which is executing program instructions, instructs 312 a measurement sensor 314 in electronic device 110 (such as a radar sensor or a radar transducer) to perform radar measurements (RM) 316 associated with an individual Note that radar measurements 316 may include information corresponding to a physiological signal of the individual, such as a vital sign of the individual (e.g., a pulse of the individual).

Then, processor 310 may analyze 318 radar measurements 316 to extract an amplitude and/or a phase of chest motion (operation 212) on or proximate to an anterior surface and/or a posterior surface of the individual. For example, analysis 318 may include demodulating the physiological response of the individual from radar measurements 316.

Moreover, processor 310 may map 320 the amplitude and/or the phase of the chest motion on or proximate to the anterior surface and/or the posterior surface to one or more anatomical locations associated with an organ of the individual. Next, processor 310 may detect 322 whether the type of arrhythmia is present and/or may determine 324 the type of arrhythmia based at least in part on the mapped amplitude and/or the phase. Note that the detection 322 and/or determination 324 may use information 326 (such as a prescription used by the individual, a medical history of the individual, etc.), which is accessed in memory 328 in electronic device 110.

When the type of arrhythmia is present, processor 310 may perform a remedial action. For example, processor 310 may instruct 332 an interface circuit 330 in electronic device 110 to: provide a report or notification to another electronic device of a medical provider, or notify emergency services (such as contacting 9-1-1). Alternatively or additionally, processor 310 may take another corrective action to eliminate the arrhythmia, such as requesting that a medical provider or professional prescribe a medication, or instructing a defibrillator to apply a corrective electric shock.

While FIG. 3 illustrates communication between components using unidirectional or bidirectional communication with lines having single arrows or double arrows, in general the communication in a given operation in this figure may involve unidirectional or bidirectional communication. Moreover, while FIG. 3 illustrates operations being performed sequentially or at different times, in other embodiments at least some of these operations may, at least in part, be performed concurrently or in parallel.

Figure 4:
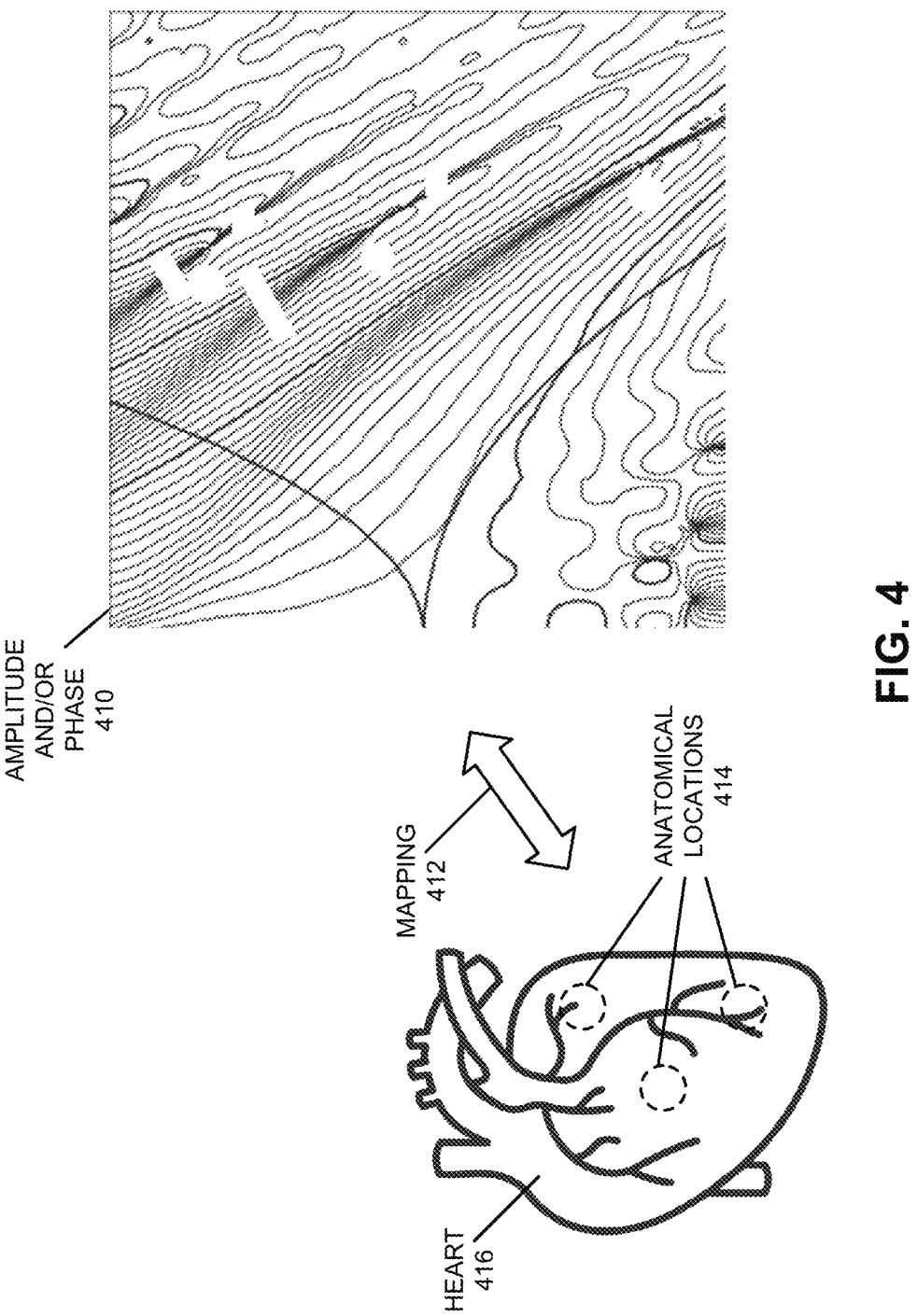
FIG. 4 is a flow diagram illustrating an example of mapping radar measurements to one or more anatomical locations in accordance with an embodiment of the present disclosure.

FIG. 4 presents a drawing illustrating an example of mapping 412 radar measurements to one or more anatomical locations 414. Notably, amplitude and/or phase 410 on or proximate to the anterior and/or the posterior surface of the individual may be mapped 412 to the one or more anatomical location 414 on a heart 416 of an individual.

In some embodiments, mapping 412 in the measurement techniques is performed using green's function. For example, a spatial pattern of the amplitude and/or the phase 410 (such as real and/or imaginary information) of the physiological signal may be mapped 412 to the one or more anatomical locations 414 by computing a source pattern at the one or more anatomical locations 414 using a Green's function calculation. In some embodiments, this inverse calculation (determining the source pattern based at least in part on the spatial pattern(s) on the posterior and/or the anterior surface of the individual is performed in the frequency domain (e.g., by performing a Fourier Transform). This may allow the convolution associated with the Green's function to be inverted more simply.

However, in other embodiments, mapping 412 is performed by a pretrained neural network. Thus, in some embodiments, the spatial patterns of the amplitude and/or the phase 410 are input to the pretrained neural network, which outputs the source pattern at the one or more anatomical locations 414. Moreover, the source pattern may be input to the same or a different pretrained neural network, which may output whether the type of arrhythmia is detected and/or the determined type of arrhythmia. Alternatively, these two operations may be combined, so that the spatial patterns of the amplitude and/or the phase 410 are input to the pretrained neural network, which outputs whether the type of arrhythmia is detected and/or the determined type of arrhythmia.

In some embodiments, the pretrained predictive model (such as the pretrained neural network) may have been trained using a training dataset with data for a cohort of, e.g., 100, 500, 1,000, 2,000 or 3,000 people. The cohort may be divided into cases (individuals with a type of arrhythmia) and controls (individuals who do not have the type of arrhythmia). For example, the training dataset may include approximately 50% cases and 50% controls. For each member of the cohort, the training dataset may include: measured amplitude and/or phase on the anterior and/or posterior chest; computed mapping of the measured amplitude and/or the phase on to one or more anatomical locations on the heart; whether the type of arrhythmia is present; when the arrhythmia is present, what the type of arrhythmia is; and, when the arrhythmia is present, the remedial action taken (if any). The pretrained predictive model may be trained using 80% of the training dataset. The remaining 20% of the training dataset may be used to test the performance of the pretrained predictive model.

As an example of the pretrained predictive model, the measurement techniques may use one or more pretrained convolutional neural networks. A large convolutional neural network may include, e.g., 60 M parameters and 650,000 neurons. The convolutional neural network may include, e.g., eight learned layers with weights, including, e.g., five convolutional layers and three fully connected layers with a final 1000-way softmax or normalized exponential function that produces a distribution over the 1000 class labels. Some of the convolution layers may be followed by max-pooling layers. In order to make training faster, the convolutional neural network may use non-saturating neurons (such as a local response normalization) and an efficient dual paral-lelized GPU implementation of the convolution operation. In addition, in order to reduce overfitting in the fully-connected layers, a regularization technique (which is some-times referred to as 'dropout') may be used. In dropout, the predictions of different models are efficiently combined to reduce test errors. In particular, the output of each hidden neuron is set to zero with a probability of 0.5. The neurons that are 'dropped out' in this way do not contribute to the forward pass and do not participate in backpropagation. Note that the convolutional neural network may maximize the multinomial logistic regression objective, which may be equivalent to maximizing the average across training cases of the log-probability of the correct label under the predic-tion distribution.

In some embodiments, the kernels of the second, fourth, and fifth convolutional layers are coupled to those kernel maps in the previous layer that reside on the same GPU. The kernels of the third convolutional layer may be coupled to all kernel maps in the second layer. Moreover, the neurons in the fully connected layers may be coupled to all neurons in the previous layer. Furthermore, response-normalization layers may follow the first and second convolutional layers, and max-pooling layers may follow both response-normal-ization layers as well as the fifth convolutional layer. A nonlinear model of neurons, such as Rectified Linear Units, may be applied to the output of every convolutional and fully-connected layer.

Moreover, in some embodiments, the first convolutional layer filters, e.g., a 224×224×3 input image with 96 kernels of size 11×11×3 with a stride of four pixels (this is the distance between the receptive field centers of neighboring neurons in a kernel map). Note that the second convolutional layer may take as input the (response-normalized and pooled) output of the first convolutional layer and may filter it with, e.g., 256 kernels of size 5×5×48. Furthermore, the third, fourth, and fifth convolutional layers may be coupled to one another without any intervening pooling or normal-ization layers. The third convolutional layer may have, e.g., 384 kernels of size 3×3×256 coupled to the (normalized, pooled) outputs of the second convolutional layer. Addition-ally, the fourth convolutional layer may have, e.g., 384 kernels of size 3×3×192, and the fifth convolutional layer may have 256 kernels of size 3×3×192. The fully-connected layers may have, e.g., 4096 neurons each. Note that the numerical values in the preceding and the remaining dis-cussion below are for purposes of illustration only, and different values may be used in other embodiments.

Furthermore, in some embodiments, the convolutional neural network is implemented using at least two GPUs. One GPU may run some of the layer parts while the other runs the remaining layer parts, and the GPUs may communicate at certain layers. The input of the convolutional neural network may be, e.g., 150,528-dimensional, and the number of neurons in the remaining layers in the convolutional neural network may be given by, e.g., 253, 440-186, 624-64, 896-64, 896-43, and 264-4096-4096-1000.

We now describe embodiments of an electronic device. FIG. 5 presents a block diagram illustrating an electronic device 500, such as electronic device 110, computer system 112, optional base station 124 or optional access point 126 in FIG. 1. This electronic device includes processing sub-system 510, memory subsystem 512, networking subsystem 514, feedback subsystem 526 and measurement subsystem 532. Processing subsystem 510 includes one or more devices configured to perform computational operations. For example, processing subsystem 510 can include one or more microprocessors, one or more application-specific integrated circuits (ASICs), one or more microcontrollers, one or more programmable-logic devices, one or more GPUs and/or one or more digital signal processors (DSPs).

Memory subsystem 512 includes one or more devices for storing data and/or instructions for processing subsystem 510 and networking subsystem 514. For example, memory subsystem 512 can include dynamic random access memory (DRAM), static random access memory (SRAM), and/or other types of memory. In some embodiments, instructions for processing subsystem 510 in memory subsystem 512 include: one or more program modules or sets of instructions (such as program instructions 522 or operating system 524), which may be executed by processing subsystem 510. Note that the one or more computer programs may constitute a computer-program mechanism. Moreover, instructions in the various modules in memory subsystem 512 may be implemented in: a high-level procedural language, an object-oriented programming language, and/or in an assem-bly or machine language. Furthermore, the programming language may be compiled or interpreted, e.g., configurable or configured (which may be used interchangeably in this discussion), to be executed by processing subsystem 510.

In addition, memory subsystem 512 can include mecha-nisms for controlling access to the memory. In some embodiments, memory subsystem 512 includes a memory hierarchy that comprises one or more caches coupled to a memory in electronic device 500. In some of these embodi-ments, one or more of the caches is located in processing subsystem 510.

In some embodiments, memory subsystem 512 is coupled to one or more high-capacity mass-storage devices (not shown). For example, memory subsystem 512 can be coupled to a magnetic or optical drive, a solid-state drive, or another type of mass-storage device. In these embodiments, memory subsystem 512 can be used by electronic device 500 as fast-access storage for often-used data, while the mass-storage device is used to store less frequently used data.

Figure 6:
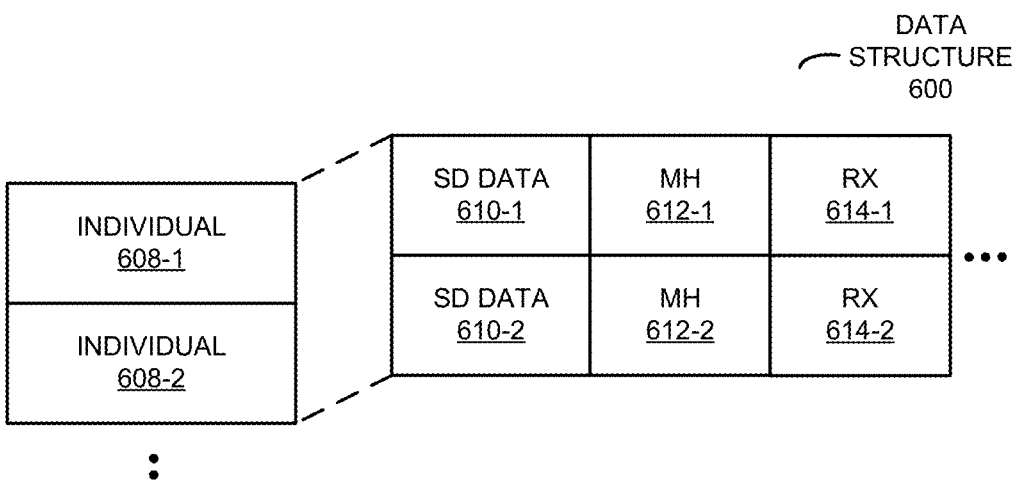
FIG. 6 is a block diagram illustrating a data structure for use in conjunction with the electronic device of FIG. 5 in accordance with an embodiment of the present disclosure.

Memory subsystem 512 may store information that is used during the measurement techniques. This is shown in FIG. 6, which presents a block diagram illustrating a data structure 600 for use in conjunction with electronic device 500 (FIG. 5). This data structure may include, for different individuals 608: information specifying socio-demographic (SD) data 610 (such as age, ethnicity, income, etc.) of the individual, information specifying a health condition or medical history (MH) 612 of the individual, one or more prescriptions (RX) 614 used by the individual, etc.

In other embodiments, the order of items in data structure 600 can vary and additional and/or different items can be included. Moreover, other sizes or numerical formats and/or data can be used.

Referring back to FIG. 5, networking subsystem 514 includes one or more devices configured to couple to and communicate on a wired and/or wireless network (i.e., to perform network operations), including: control logic 516, an interface circuit 518, one or more antennas 520 and/or input/output (I/O) port 530. (While FIG. 5 includes one or more antennas 520, in some embodiments electronic device 500 includes one or more nodes 508, e.g., a pad, which can be coupled to one or more antennas 520. Thus, electronic device 500 may or may not include one or more antennas 520.) For example, networking subsystem 514 can include a Bluetooth networking system, a cellular networking system (e.g., a 3G/4G/5G network such as UMTS, LTE, etc.), a universal serial bus (USB) networking system, a networking system based on the standards described in IEEE 802.11 (e.g., a Wi-Fi networking system), an Ethernet networking system, and/or another networking system.

In some embodiments, a transmit antenna radiation pattern of electronic device 500 may be adapted or changed using pattern shapers (such as reflectors) in one or more antennas 520 (or antenna elements), which can be independently and selectively electrically coupled to ground to steer the transmit antenna radiation pattern in different directions. Thus, if one or more antennas 520 includes N antenna-radiation-pattern shapers, the one or more antennas 120 may have $2^N$ different antenna-radiation-pattern configurations. More generally, a given antenna radiation pattern may include amplitudes and/or the phases of signals that specify a direction of the main or primary lobe of the given antenna radiation pattern, as well as so-called 'exclusion regions' or 'exclusion zones' (which are sometimes referred to as 'notches' or 'nulls'). Note that an exclusion zone of the given antenna radiation pattern includes a low-intensity region of the given antenna radiation pattern. While the intensity is not necessarily zero in the exclusion zone, it may be below a threshold, such as 3 dB or lower than the peak gain of the given antenna radiation pattern. Thus, the given antenna radiation pattern may include a local maximum (e.g., a primary beam) that directs gain in the direction of an electronic device that is of interest, and one or more local minima that reduce gain in the direction of other electronic devices that are not of interest. In this way, the given antenna radiation pattern may be selected so that communication that is undesirable (such as with the other electronic devices) is avoided to reduce or eliminate adverse effects, such as interference or crosstalk.

Networking subsystem 514 includes processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for the network system. Moreover, in some embodiments a 'network' between the electronic devices does not yet exist. Therefore, electronic device 500 may use the mechanisms in networking subsystem 514 for performing simple wireless communication between the electronic devices, e.g., transmitting advertising or beacon frames and/or scanning for advertising frames transmitted by other electronic devices as described previously.

Within electronic device 500, processing subsystem 510, memory subsystem 512, and networking subsystem 514 are coupled together using bus 528. Bus 528 may include an electrical, optical, and/or electro-optical connection that the subsystems can use to communicate commands and data among one another. Although only one bus 528 is shown for clarity, different embodiments can include a different number or configuration of electrical, optical, and/or electro-optical connections among the subsystems.

In some embodiments, electronic device 500 includes a feedback subsystem 526 that provides or presents information (such as a user interface, an augmented or a virtual reality image, a recommendation, etc.) to a user of electronic device 500. For example, feedback subsystem 526 may include a display subsystem that displays the information on a display, which may include a display driver and the display, such as a liquid-crystal display, a multi-touch touchscreen, etc.

In some embodiments, electronic device 500 includes a measurement subsystem 532 may include one or more types of measurement sensors or transducers, such as one or more image sensors and/or one or more radar sensors or radar transducers configured to transmit radar signals and to perform radar measurements. For example, measurement subsystem 532 may include or may use: control logic, one or more radar transceivers that are collocated in electronic device 500, and a set of one or more antennas (or antenna elements) that are electrically coupled to radar transceivers at antenna nodes (such as, e.g., one or more connectors or pads). These radar transceivers may or may not be synchronized with each other. Note that measurement subsystem 532 may acquire or capture one or more images (with 2D or 3D information.

Electronic device 500 can be (or can be included in) any electronic device with at least one network interface. For example, electronic device 500 can be (or can be included in): a desktop computer, a laptop computer, a subnotebook/netbook, a server, a mainframe computer, a cloud-based computer system, a tablet computer, a smartphone, a cellular telephone, a smart watch, a headset, electronic or digital glasses, headphones, a consumer-electronic device, a portable computing device, an access point, a router, a switch, communication equipment, test equipment, a wearable device or appliance, a headset, a display, and/or another electronic device.

Although specific components are used to describe electronic device 500, in alternative embodiments, different components and/or subsystems may be present in electronic device 500. For example, electronic device 500 may include one or more additional processing subsystems, memory subsystems, networking subsystems, feedback subsystems (such as an audio subsystem) and/or measurement subsystem. Additionally, one or more of the subsystems may not be present in electronic device 500. Moreover, in some embodiments, electronic device 500 may include one or more additional subsystems that are not shown in FIG. 5. Also, although separate subsystems are shown in FIG. 5, in some embodiments, some or all of a given subsystem or component can be integrated into one or more of the other subsystems or component(s) in electronic device 500. For example, in some embodiments program instructions 522 are included in operating system 524.

Moreover, the circuits and components in electronic device 500 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 514 (such as a radio) and/or measurement subsystem 532. Moreover, the integrated circuit may include hardware and/or software mechanisms that are used for transmitting wireless signals from electronic device 500 and receiving signals at electronic device 500 from other electronic devices. Aside from the mechanisms herein described, radios are generally known in the art and hence are not described in detail. In general, networking subsystem 514 and/or the integrated circuit can include any number of radios. Note that the radios in multiple-radio embodiments function in a similar way to the described single-radio embodiments.

In some embodiments, networking subsystem 514 and/or the integrated circuit include a configuration mechanism (such as one or more hardware and/or software mechanisms) that configures the radio(s) to transmit and/or receive on a given communication channel (e.g., a given carrier frequency). For example, in some embodiments, the configuration mechanism can be used to switch the radio from monitoring and/or transmitting on a given communication channel to monitoring and/or transmitting on a different communication channel. (Note that 'monitoring' as used herein comprises receiving signals from other electronic devices and possibly performing one or more processing operations on the received signals, e.g., determining if the received signal comprises an advertising frame, receiving the input data, etc.)

While communication protocols compatible with Ethernet, Wi-Fi and a cellular-telephone communication protocol were used as illustrative examples, the described embodiments of the measurement techniques may be used in a variety of network interfaces. Furthermore, while some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both. For example, at least some of the operations in the measurement techniques may be implemented using program instructions 522, operating system 524 (such as a driver for interface circuit 518) and/or in firmware in interface circuit 518. Alternatively or additionally, at least some of the operations in the measurement techniques may be implemented in a physical layer, such as hardware in interface circuit 518.

Additionally, while the preceding embodiments illustrated the use of wireless signals in one or more bands of frequencies, in other embodiments of these signals may be communicated in one or more bands of frequencies, including: a microwave frequency band, a radar frequency band, 900 MHz, 2.4 GHz, 5 GHz, 6 GHz, 7 GHz, 60 GHz, and/or a band of frequencies used by a Citizens Broadband Radio Service (CBRS) or by LTE. In some embodiments, the communication between electronic devices uses multi-user transmission (such as OFDMA).

In the preceding description, we refer to 'some embodiments.' Note that 'some embodiments' describes a subset of all of the possible embodiments, but does not always specify the same subset of embodiments. Moreover, note that the numerical values provided are intended as illustrations of the measurement techniques. In other embodiments, the numerical values can be modified or changed.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. An electronic device, comprising:
a measurement sensor;
a computation device, coupled to the measurement device and memory, configured to execute program instructions;
the memory configured to store the program instructions, wherein, when executed by the computation device, the program instructions cause the electronic device to perform one or more operations comprising:
performing, using the measurement sensor, radar measurements associated with an individual, wherein the radar measurements comprise information corresponding to a physiological signal of the individual;
analyzing the radar measurements to extract an amplitude and/or a phase of chest motion on or proximate to an anterior surface and/or a posterior surface of the individual;
mapping the amplitude and/or the phase of the chest motion on or proximate to the anterior surface and/or the posterior surface to one or more anatomical locations associated with an organ of the individual; and
detecting whether a type of arrhythmia is present based at least in part on the mapped amplitude and/or the phase.

2. The electronic device of claim 1, wherein the physiological signal comprises a vital sign of the individual.

3. The electronic device of claim 1, wherein the type of arrhythmia comprises: atrial fibrillation, tachycardia, bradycardia, or a type of heart attack.

4. The electronic device of claim 1, wherein the radar measurements are associated with the anterior surface and/or the posterior surface of the individual;
wherein the measurement sensor comprises multiple radar sensors or radar transducers at different locations and having different transmission directions.

5. The electronic device of claim 4, wherein the radar measurements are performed synchronously; and
wherein the operations comprise comparisons of the amplitude and/or the phase of the chest motion on or proximate to the anterior surface and/or the posterior surface of the individual corresponding to the synchronous radar measurements.

6. The electronic device of claim 5, wherein the synchronous radar measurements are performed with a time accuracy or difference on or proximate to the anterior surface and/or the posterior surface of less than a predefined amount of a pulse rate of the individual.

7. The electronic device of claim 1, wherein the analysis comprises demodulating the radar measurements to obtain the physiological signal of the individual.

8. The electronic device of claim 1, wherein the analysis is performed by the electronic device.

9. The electronic device of claim 1, wherein the electronic device comprises an interface circuit configured to communicate with a computer system;

wherein performing the analysis comprises:

providing, to the computer system, second information specifying the radar measurements; and receiving, from the computer system, third information specifying the physiological signal.

10. The electronic device of claim 1, wherein the organ comprises a heart of the individual; and wherein the mapping comprises mapping the amplitude and/or the phase on or proximate to the anterior surface and/or the posterior surface of the individual to one or more anatomical locations associated with the heart of the individual.

11. The electronic device of claim 1, wherein the mapping comprises a three-dimensional transformation.

12. The electronic device of claim 1, wherein, when the type of arrhythmia is detected, the operations comprise providing second information specifying the type of arrhythmia.

13. The electronic device of claim 12, wherein the providing of the second information comprises displaying a graphical representation of the mapping to one or more anatomical locations associated with a heart of the individual.

14. The electronic device of claim 1, wherein the mapping is performed using a pretrained predictive model.

15. The electronic device of claim 14, wherein the pretrained predictive model comprises a pretrained neural network; and wherein spatial patterns of the amplitude and/or the phase on or proximate to the anterior and/or posterior surface are input to the pretrained neural network, and an output of the pretrained neural network comprises whether or not the arrhythmia is present and/or the type of the arrhythmia.

16. The electronic device of claim 15, wherein the output comprises a confidence of the detected presence of and/or the type of the arrhythmia.

17. The electronic device of claim 1, wherein the operations comprise detecting a type of fall by the individual.

18. The electronic device of claim 17, wherein the type of fall comprises one or more of: whether the individual has fallen, a direction of the fall, whether the individual attempted to break or arrest their fall, whether the individual hit their head when they fell, or how fast the individual was moving when their fall was arrested.

19. A non-transitory computer-readable storage medium for use in conjunction with an electronic device, the computer-readable storage medium configured to store program instructions that, when executed by the electronic device, cause the electronic device to perform one or more operations comprising:

performing, using a measurement sensor, radar measurements associated with an individual, wherein the radar measurements comprise information corresponding to a physiological signal of the individual;

analyzing the radar measurements to extract an amplitude and/or a phase of chest motion on or proximate to an anterior surface and/or a posterior surface of the individual;

mapping the amplitude and/or the phase of the chest motion on or proximate to the anterior surface and/or the posterior surface to one or more anatomical locations associated with an organ of the individual; and detecting whether a type of arrhythmia is present based at least in part on the mapped amplitude and/or the phase.

20. A method for remotely assessing an individual for a presence of a type of arrhythmia, comprising:

by an electronic device:

performing, using a measurement sensor, radar measurements associated with the individual, wherein the radar measurements comprise information corresponding to a physiological signal of the individual;

analyzing the radar measurements to extract an amplitude and/or a phase of chest motion on or proximate to an anterior surface and/or a posterior surface of the individual;

mapping the amplitude and/or the phase of the chest motion on or proximate to the anterior surface and/or the posterior surface to one or more anatomical locations associated with an organ of the individual; and detecting whether the type of arrhythmia is present based at least in part on the mapped amplitude and/or the phase.

\* \* \* \* \*